(12) United States Patent
Ishida et al.

(10) Patent No.: US 8,137,297 B2
(45) Date of Patent: Mar. 20, 2012

(54) CORRECTIVE DEVICE FOR DEFORMED NAILS

(75) Inventors: Kiyohito Ishida, Miyagi (JP); Kiyoshi Yamauchi, Miyagi (JP); Ryosuke Kainuma, Miyagi (JP); Yuji Sutou, Miyagi (JP); Toshihiro Omori, Miyagi (JP); Akira Ogawa, Saitama (JP)

(73) Assignee: Tohoku University, Miyagi (JP)

( * ) Notice: Subject to any disclaimer, the term of this patent is extended or adjusted under 35 U.S.C. 154(b) by 646 days.

(21) Appl. No.: 12/223,981

(22) PCT Filed: Dec. 20, 2006

(86) PCT No.: PCT/JP2006/325988
§ 371 (c)(1),
(2), (4) Date: Sep. 19, 2008

(87) PCT Pub. No.: WO2007/094125
PCT Pub. Date: Aug. 23, 2007

(65) Prior Publication Data
US 2010/0228173 A1    Sep. 9, 2010

(30) Foreign Application Priority Data

Feb. 14, 2006 (JP) .................... 2006-036495
Feb. 14, 2006 (JP) .................... 2006-036496

(51) Int. Cl.
*A61F 5/00* (2006.01)
(52) U.S. Cl. ............................ 602/30; 602/31
(58) Field of Classification Search .............. 602/30–31; 128/882; 132/73, 73.5, 75.8, 76.2
See application file for complete search history.

(56) References Cited

U.S. PATENT DOCUMENTS

| 3,173,416 A | * | 3/1965 | Rederich ................ 602/31 |
| 5,850,837 A | | 12/1998 | Shiroyama et al. |
| 6,050,966 A | * | 4/2000 | Wilberscheid ............ 602/31 |

FOREIGN PATENT DOCUMENTS

| JP | 8-215227 | 8/1996 |
| JP | 9-253110 | 9/1997 |

(Continued)

OTHER PUBLICATIONS

International Search Report mailed Mar. 6, 2007 for International Application No. PCT/JP2006/325988. Supplementary European Search Report dated Mar. 19, 2010 in corresponding European Application No. 06843371.3.

*Primary Examiner* — Michael A. Brown
(74) *Attorney, Agent, or Firm* — Wenderoth, Lind & Ponack, L.L.P.

(57) ABSTRACT

An elastic metal strip aligning a longitudinal direction with a rolling direction of a cold-rolled plate is collected and processed to a shape including a correction plate with the longitudinal direction of the elastic metal as a width direction of a nail and a plurality of tongue strips protruded from the edge of the correction plate near the nail tip. Each tongue strip is folded and bent to form a hooked claw with a double structure of a folding part and a bending part. A nail tip of a deformed nail is inserted between the hooked claw and the correction plate to apply a restoring force of elasticity in the correction plate to the deformed nail as correction ability for deformed nails. A wrought wire rod can be used instead of a cold-rolled plate and a Cu—Al—Mn type shape-memory alloy may further be used as a raw material.

15 Claims, 7 Drawing Sheets

FOREIGN PATENT DOCUMENTS

| | | |
|---|---|---|
| JP | 2001-37535 | 2/2001 |
| JP | 2001-276104 | 10/2001 |
| JP | 2002-360619 | 12/2002 |
| JP | 2003-10218 | 1/2003 |
| JP | 2003-265508 | 9/2003 |
| JP | 2005-296569 | 10/2005 |
| JP | 2006-314748 | 11/2006 |
| JP | 2007-185203 | 7/2007 |

* cited by examiner

FIG.1

(PRIOR ART)

CORRECTIVE DEVICE FOR DEFORMED NAILS

FIELD OF THE INVENTION

The present invention relates to a corrective device readily worn on deformed nails such as ingrown nails, ingrown toenails and the like and used for eliminating the deformation, and a manufacturing method thereof.

RELATED ART

Various corrective devices for deformed nails have been conventionally proposed to correct ingrown nails, ingrown toenails and the like. For example, there is a corrective device for ingrown nails that entails gluing a small strip with an appropriate restoring force onto a surface of an ingrown nail, and gradually correcting ingrown nails to normal configuration (Patent Document 1), a corrective device for ingrown nails that entails providing an elastic force to a pair of hooked ends of the device grappled at the edge across the width of the deformed nail to pull (Patent Document 2), a corrective device that applies a tensile force in the direction opposite to the deformation direction to both edges of a nail (Patent Document 3) and the like.

A corrective device for ingrown toenails manufactured from a shape-memory alloy has also been known (Patent Document 4). The corrective device made from a shape-memory alloy has been transformed to a configuration different from the shape provided in a shape-memorization process and worn on the ingrown toenail and a force intending to restore to an original shape is utilized as a corrective force. Ni—Ti type alloys, Cu—Zn type alloys and Cu—Al—Ni type alloys are used as a shape-memory alloy.

Patent Document 1: Japanese Patent Publication No. 2001-37535A
Patent Document 2: Japanese Patent Publication No. 2003-265508A
Patent Document 3: Japanese Patent Publication No. 2001-276104A
Patent Document 4: Japanese Patent Publication No. H09-253110A In a method to glue a corrective device to a nail surface, the end of the corrective device in the width direction of a nail is likely to curl and peel. An adhesive used in gluing may seep between a nail and a corrective device, causing a user tremendous discomfort and the adhesive will have to be eliminated from a nail surface after releasing the corrective device, thus causing a user to avoid using of the adhesion-type corrective device.

In a corrective device in which tensile force is applied to a hooked end or locking part grappled at the edge across the width of a deformed nail, the hooked end or locking part has to be inserted into the edge across the width of a deformed nail, giving a patient pain, which is a drawback. A process such as drilling a mounting hole for a locking part in part of the deformed nail and the like is required, depending on a type of the corrective device and is difficult for a patient to wear and release by himself.

A method of engaging the hooked end of a corrective device with a nail may be considered in order to facilitate wearing and releasing the corrective device. However, a general method of engaging the hooked end has to increase deformation resistance of the hooked end in order to prevent an angle between the hooked end and the correction plate from increasing.

A corrective device for deformed nails using a shape-memory alloy as a raw material utilizes soft super-elastic characteristics provided to the shape-memory alloy in order to stably apply the required corrective force to a nail without causing pain. While the shape-memory effect and the super-elastic effect of a shape-memory alloy are the phenomenon accompanied by transformation and reverse transformation of a martensite generated by thermal induction and stress induction, respectively, a Ni—Ti type shape-memory alloy is very large in an entropy change accompanied by the transformation and reverse transformation of a martensite, resulting in large fluctuation of the deformation stress and recovery stress (corrective force) with a temperature change.

Wide fluctuation of the deformation stress and recovery stress provides pain to a patient wearing the corrective device. A Cu—Zn type alloy heavily deteriorates with environmental changes, making it difficult to wear a corrective device for a long period of time and a Cu—Al—Ni type alloy is extremely brittle and cannot be processed to a desired shape of a corrective device.

SUMMARY OF THE INVENTION

The present inventors have focused attention on easiness of wearing and releasing such a type of corrective device as engaging the hooked end of a correction plate with a deformed nail and investigated in many ways a means to prevent an angle between the correction plate and the hooked end from widening. As a result, they found that when the plate is folded and bent to a double fold instead of simple hook, forming a hooked claw, an angle between the corrective plate and the hooked end can be kept nearly constant, enabling the correction plate to be stably worn on a deformed nail.

The present invention has a first object to provide a corrective device for deformed nails of stabilizing a wearing state over a long period of time, as well as facilitating wearing and releasing by providing a hooked claw with a double-folded construction to the edge of a correction plate near the nail tip or both ends of a correction plate across the nail width, after focusing attention on effectiveness of a hooked claw formed by such a double fold for stably wearing a corrective device.

A second object is also to provide a corrective device for deformed nails of facilitating wearing and releasing, as well as improving the correction ability by forming a similar hooked claw on a corrective device for deformed nails manufactured from a Cu—Al—Mn type shape-memory alloy, in which the shape-memory ability is higher in the width direction of a nail and the deformation stress is increased in the direction of a nail tip.

A third object is to further increase the shape-memory ability, and consequently, the correction ability for deformed nails, in a corrective device for deformed nails by growing a recrystallization texture oriented to a specific direction with heat treatment after forming a hooked claw using as a raw material a cold-rolled material of a Cu—Al—Mn type shape-memory alloy.

A corrective device for deformed nails corresponding to the first object is manufactured by cutting or punching and bending an elastic metal plate, comprising a correction plate and a plurality of hooked claws engaged with a nail tip. The corrective plate is aligned in its longitudinal direction with the width direction of a nail. The hooked claw is provided with a double structure of a folding part and a bending part formed by folding and bending a tongue strip protruded from the edge of a correction plate near the nail tip or both ends of a correction plate across the nail width.

A planar cold-rolled plate manufactured in a cold roll and a wrought wire rod obtained by cold pressing to flatten a round wire rod, can be used as a raw material for a correction plate. In a corrective device using a cold-rolled plate as a raw material, a hooked claw is formed by double-folding of a tongue strip protruded from the edge of a corrective plate near the nail tip. In a hooked claw in the corrective device using a wrought wire rod as a raw material, the hooked claw is formed by double-folding of both ends of the correction plate across the nail width. A wrought wire rod pressed to a flattened shape may be treated as a kind of a cold-rolled plate from a viewpoint of its aggregate texture of {112}<110> orientation.

A corrective device for deformed nails corresponding to the second object is the corrective device using as a raw material a cold-rolled plate, a wrought wire rod and the like of a Cu—Al—Mn type shape-memory alloy having a recrystallization texture comprising a substantially single phase with uniform crystal orientation. The corrective device is provided with a correction plate having a tongue strip protruded from the edge near the nail tip or a protruding part at both ends across the nail width, in which a cold-rolled material is cut out in the rolling direction as the longitudinal direction to form a nearly rectangular metal band with the longitudinal direction being the width direction of a nail. A hooked claw is similarly formed by double-folding of the tongue strip or protruding part as the first corrective device for deformed nails. The width direction of a nail in the correction plate is aligned with the rolling direction of a cold-rolled material, thereby giving shape-memorization ability in relation to the width direction of a nail and increasing the deformation stress in the direction of a nail tip.

When increasing shape-memorization ability of a Cu—Al—Mn type shape-memory alloy, and consequently, its correction ability for deformed nails, a hooked claw with a double structure of a folding part and a bending part is formed by folding and bending a tongue strip or protruding part, followed by heat treatment for shape-memorization or superelasticity to orient the principal direction of a recrystallized 13 phase to the {112}<110> orientation.

DETAILED DESCRIPTION OF THE INVENTION

A metal band cut out from a cold-rolled plate, a cold-rolled plate collected from a wrought wire rod, a cold-rolled material of a Cu—Al—Mn type shape-memory alloy and the like are used as raw materials of a corrective device for deformed nails. A hooked claw with a double structure formed by folding and bending is adapted as a corrective device manufactured from each raw material, facilitating wear and release, while proving high correction ability for a deformed nail. A corrective device using a Cu—Al—Mn type shape-memory alloy as a raw material is intended to improve shape-memory characteristics (correction ability for deformed nail) without detriment to the power of the hooked claw for engaging with a nail tip by treatment for shape-memorization or heat treatment for super-elasticity after forming the hooked claw to orient the principal direction of the recrystallized 13 phase to {112}<110> orientation.

The double-folded hooked claw is dramatically stabilized when wearing on a deformed nail as compared with a nail locking part formed by simple folding used in a conventional corrective device. Comparison of properties of a double-folded hooked claw with those of a nail locking part formed by simple folding can be described as follows.

When a conventional corrective device (FIG. 1), in which the edge of a correction plate 1 is simply bent as a nail locking part 2 is worn on a deformed nail 20, the nail locking part 2 contacts with a nail tip 21 through only one point $P_1$. A contact point $P_1$ between the nail locking part 2 and the nail tip 21 is limited to one point because of a simple method of forming the nail locking part 2.

Figure 1:
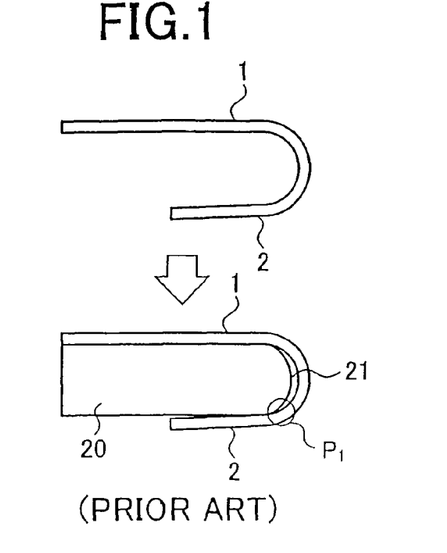
FIG. 1 is a view illustrating a drawback of a conventional corrective device for deformed nails in which the edge of a correction plate is simply bent to form the locking part for a nail.

A hooked nail locking part 2 from a correction plate 1 is parallel with the correction plate 1 when not being worn on a deformed nail 20, but contacts with a nail tip 21 at one contact point $P_1$ to open in a certain angle of inclination when inserting the nail tip 21 of the deformed nail 20 between the correction plate 1 and the nail locking part 2. The retaining force holding the nail locking part 2 is weak because of the one point contact, making it difficult to obtain a stable wearing condition. Opening of the nail locking part 2 near the nail root is likely to cause entry of foreign substances into a gap between the nail locking part 2 and the deformed nail 20, loosening the nail locking part 2 upward. When a gap of the nail locking part 2 is narrowed in the open side in order to increase wearability, the correction plate is difficult to wear on the deformed nail 20, so narrowing of the gap is limited.

In a corrective device of the present invention (FIG. 2), in which a hooked claw 6 is formed by double folding a tongue strip protruded from a correction plate 1, two planes are partitioned, respectively, by a folding part 4 and a bending part 5, thus generating a step between the edge of the folding part 4 and the bending part 5. When a deformed nail 20 is inserted between this hooked claw 6 and the correction plate 1, the hooked claw 6 contacts with a nail tip 21 of a deformed nail 20 at two points, $P_1$ and $P_2$, at part of the inner face of the bending part 5 and the edge of the folding part 4.

Figure 2:
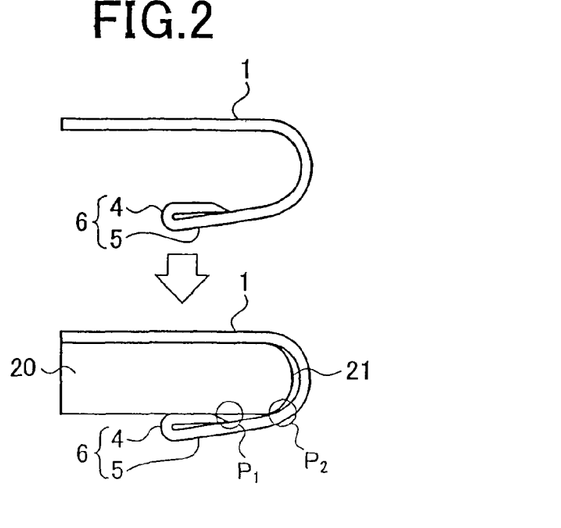
FIG. 2 is a view illustrating the function of a hooked claw formed by double folding of a tongue strip protruded from a correction plate.

Contact at two points $P_1$ and $P_2$ drastically improves wearing stability as compared with a corrective device with a simple hook (FIG. 1). A double-folded structure further increases an effective wall thickness of a hooked claw 6 and increases deformation stress (spring back force) of the hooked claw 6 with respect to a direction of a nail tip, thus increasing a force to retain a deformed nail 20. Increase of deformation stress means higher shape stability of the hooked claw 6 and squeezing the tip of a folding part 4 between a correction plate 1 and a bending part 5 is also effective to prevent the hooked claw 6 from deformation. A corrective device is thus stably worn over a long period of time, improving a corrective effect on the deformed nail 2. A sharp edge of the hooked claw 6 is not exposed outside, thus preventing a nail tip 21 and a finger tip from injury.

Example 1

A hooked claw 6 (FIG. 2) and a nail stopping part 2 of a simple hook (FIG. 1) with a length of 3 mm were formed on a short rectangular strip with length of 6.4 mm and width of 2.2 mm cut out from an SUS 304 stainless steel plate with thickness of 0.2 mm in order to compare the effect of a double fold and a simple hook on correction ability for deformed nails and a holding force of a nail. A curvature radius of bending from a corrective plate 1 was made to be approximately 0.475 mm in both the hooked claw 6 and the nail stopping part 2, and a gap between the nail stopping part 2 and the correction plate 1 and a gap between a folding part 4 and the correction plate 1 were chosen to be 0.95 mm, respectively.

Using an aluminum plate with a plate thickness of 1.02 mm as a virtual nail, the edge of the aluminum plate was sandwiched between a correction plate 1 and a hooked claw 6 or between a correction plate 1 and a nail stopping part 2, respectively, to measure a load of pulling out the hooked claw 6 or nail stopping part 2 from a nail tip. A minimum load required for pullout was 120 g in a corrective device with a hooked claw 6 and 70 g in a corrective device with a nail stopping part 2, respectively. It is understood from the large difference in pullout force, that a double structure of a hooked claw 6 has a very large nail holding force as compared with a nail stopping part 2 with a simple hook.

Next, a corrective device for a deformed nail using a metal band cut out from a cold-rolled plate is described in detail.

Figure 5:
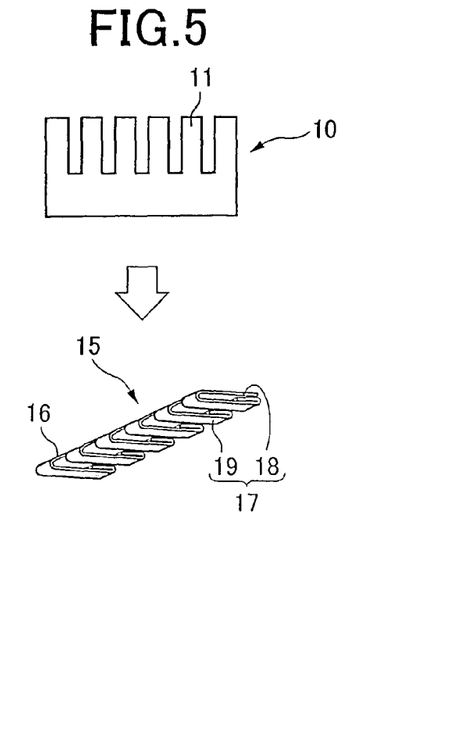
FIG. 5 is a diagram illustrating a manufacture process of a corrective device in which a plurality of hooked claws is disposed in equal space along the width direction of a nail.
Figure 7:
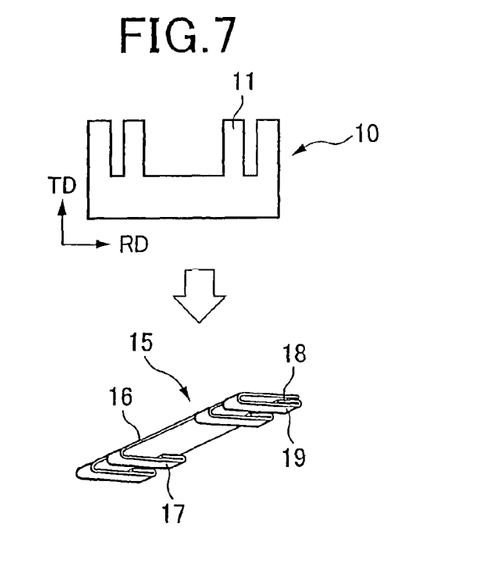
FIG. 7 is a diagram illustrating a manufacture process of a corrective device provided with a plurality of hooked claws in the vicinity of both ends across the nail width.

A corrective device for a deformed nail in the present example uses as a raw material an elastic metal strip 10 in which a cold-rolled plate of an elastic metal material was cut out or punched out. The elastic metal strip 10 has a size equal to or smaller than the length across the width of a deformed nail, and a plurality of tongue strips 11 protrude from the edge near the nail tip. The tongue strips 11 may be located either in the vicinity of the central part along a length direction of the elastic metal strip 10 (FIG. 3) or in the vicinity of both ends in a length direction (FIG. 7). Or a plurality of tongue strips 11 may be formed at even intervals along a length direction of the elastic metal strip 10 (FIG. 5).

Ordinary steels, alloy steels, stainless steel, copper alloys, titanium, titanium alloys, cobalt alloys, shape-memory alloys and the like can be used as materials of an elastic metal strip 10 as far as they have an elastic force. When a material that may cause inflammation with a metal ion is used as the elastic metal strip 10, the elastic metal strip 10 is surface-treated or a metal surface is coated with plated scraps, a plastic film and the like. Before collecting the elastic metal strip 10, a raw material metal plate is hardened to increase an elastic force. Hardening includes process hardening, quench hardening, transformation hardening, age hardening, deposition hardening and the like.

A tongue strip 11 protruded from the edge of an elastic metal strip across the nail tip is folded and bent to form a plurality of hooked claws 17 with a double structure of a folding part 18 and a bending part 19. The hooked claw 17 is the part to engage with a nail tip 21 of a deformed nail 20.

Figure 3:
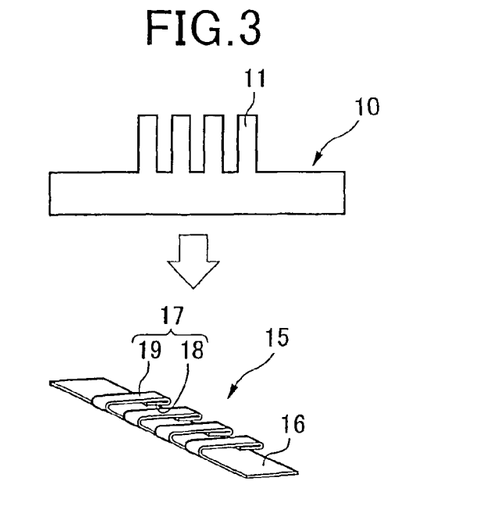
FIG. 3 is a diagram illustrating a manufacture process of a corrective device with a plurality of hooked claws at a central part across the nail width.
Figure 4A:
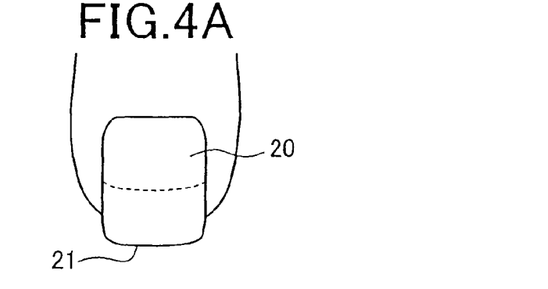
FIG. 4A is a plain view of an elongated deformed nail.
Figure 4B:
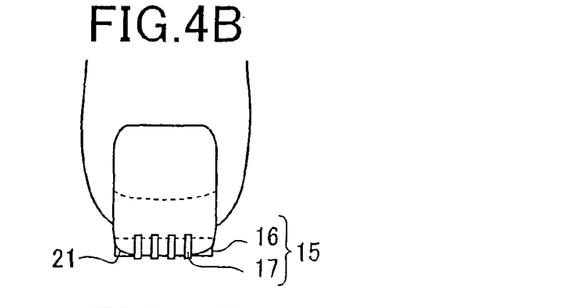
FIG. 4B is a plain view of a deformed nail wearing a corrective device in FIG. 3, by inserting a hooked claw between a finger tip and a nail tip.
Figure 4C:
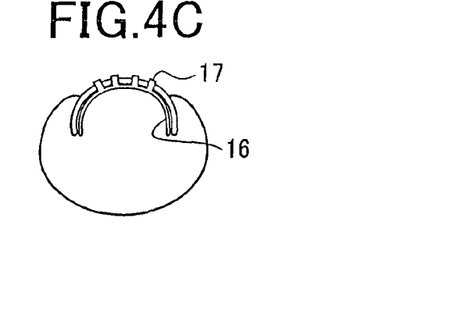
FIG. 4C is an elevation view of a state of wearing the same.

A corrective device 15 (FIG. 3) with a plurality of hooked claws 17 at the central part across the nail width is suitable for patients having long nails (FIG. 4A). The hooked claw 17 is slightly pulled away from a correction plate 16 and a correction plate 16 deflected is inserted between a finger tip and a nail tip 21. Once a force applied to the hooked claw 17 is released, the hooked claw 17 is pressed to the outside of the nail tip 21, fixing the corrective device 15 onto the nail tip 21 (FIGS. 4B and 4C). A restoring force of elasticity for the correction plate 16 to return to an original shape in a state of pinching the central part across the width with the correction plate 16 and the hooked claw 17 acts from inside on a deformed nail 20 in the vicinity of both ends across the nail width. A restoring force of elasticity thus efficiently works as correction ability of the deformed nail to correct the deformed nail 20.

Figure 6A:
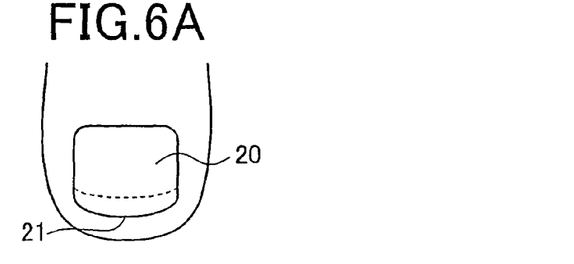
FIG. 6A is a plain view of a short deformed nail.
Figure 6B:
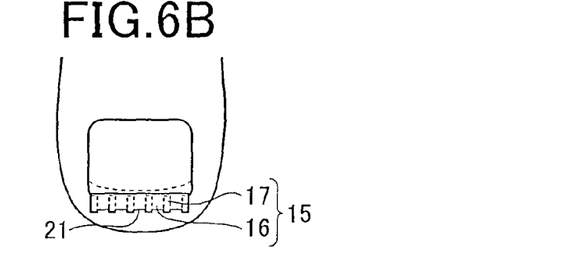
FIG. 6B is a plain view of a deformed nail wearing a corrective device in FIG. 5, by inserting a hooked claw between a finger tip and a nail tip.
Figure 6C:
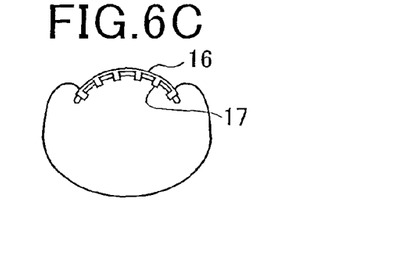
FIG. 6C is an elevation view of a state of wearing the same.

A corrective device 15 (FIG. 5), provided with a plurality of hooked claws 17 at even intervals along the width direction of nail, is suitable for patients with a deformed nail 20 of an ordinary length (FIG. 6A). A correction plate 16 is slightly deflected and a hooked claw 17 is inserted between a finger tip and a nail tip 21 to put the correction plate 16 on the outside of the nail tip 21, thereby fixing the corrective device 15 onto the nail tip 21 (FIGS. 6B and 6C). In this case, a folding part 18 is pressed from inside to the nail tip 21 so that the nail tip 21 is pinched between the correction plate 16 and the hooked claw 17 for retention. Since the nail tip 21 is sandwiched between the correction plate 16 and the hooked claw 17 placed at even intervals along the width direction of nail, a restoring force of elasticity in the correction plate 16 acts as correction ability for a deformed nail throughout the length of a deformed nail 20 across the nail width, thereby correcting the deformed nail 20. Length of the corrective device 15 is also shortened in the width direction of nail, enabling to correct only the deformed part of the deformed nail 20. This type of a corrective device is suitable for patients with a short deformed nail 20.

Figure 8A:
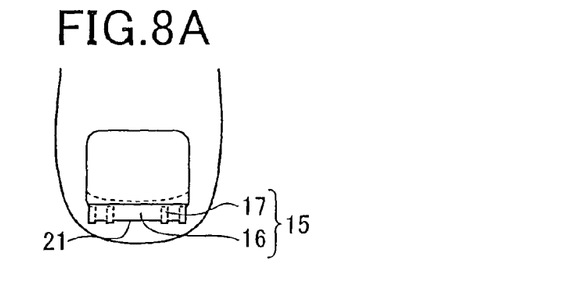
FIG. 8A is a plain view of a deformed nail wearing a corrective device in FIG. 7 by inserting a hooked claw between a finger tip and a nail tip and FIG. 8B is a front view of a state of wearing the same.
Figure 8B:
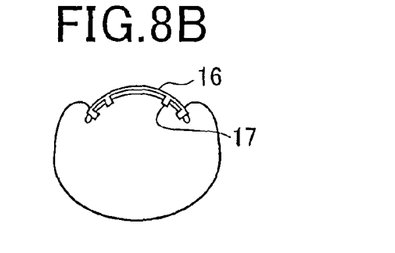

A hooked claw 17(FIG. 7), may be provided in the vicinity of both ends across the nail width, instead of providing a plurality of hooked claws 17 at even intervals along the width direction of nail. A correction plate 16 is deflected and the hooked claw 17 is inserted between a finger tip and a nail tip 21 to place the correction plate 16 along the outer surface of a nail tip 21, thereby pinching the nail tip 21 in the vicinity of both ends across the nail width between the correction plate 16 and the hooked claw 17 for retention (FIGS. 8A and 8B). A restoring force of elasticity in the correction plate 16, acts on a deformed nail across the nail width, in a state of restricting both ends of a deformed nail 20 across the nail width, thereby correcting the deformed nail 20 similarly as a corrective device 15 in FIG. 5.

Since a plurality of hooked claws 17 is formed along the edge of a correction plate near the nail tip in any one of corrective devices 15 in FIGS. 3, 5 and 7, the effect of the hooked claw 17 on deflection deformation of a correction plate 16 across the nail width can be neglected. The correction plate 16 is therefore relatively readily bent in relation to a longitudinal direction (width direction of nail) and a restoring force of elasticity acts on a deformed nail as a corrective force.

A correction plate 16 may be any one of a flat shape or slightly curved shape corresponding to a nail tip. A curved shape can be obtained by providing a correction plate 16 with a curvature corresponding to a shape of a deformed nail 20 when forming a hooked claw 17 or before or after forming a hooked claw 17.

When a hooked claw 17 remains as it is formed, there are cases in which an elastic metal strip 10 cannot keep its desired shape due to spring back. Stress and strain introduced in the bending process are also likely to cause loss of the shape in a corrective device 15. Annealing for removal of strain is therefore performed if desired before or after formation of the hooked claw 17. Bluing treatment is also possible depending on a condition of thermal treatment, further increasing an elastic limit. A condition of heat treatment varies with a material for an elastic metal strip 10, but in a case of using a stainless steel as a raw material, bluing treatment by heating at a temperature range of 200 to 600° C. and annealing for removal of strain by heating at a temperature range of 600 to 800° C. are intended to improve shape stability and correction ability for a deformed nail in a corrective device 15. A heating temperature at 200° C. or higher is required to achieve the effect of heat treatment, but high temperature heating at 800° C. or higher softens an elastic metal strip 10 and raises concern about decrease of an elastic force.

A hooked claw 17 provided along a longitudinal direction (width direction of the nail) of a correction plate 16 allows the correction plate 16 to bend in the width direction of the nail, facilitating wearing of a corrective device 15. After wearing, a plurality of hooked claws 17 are engaged with a nail tip of a deformed nail 20 and both ends of the correction plate 16 (FIG. 3) are pressed from inside by a restoring force of elasticity to both ends of deformed nail 20 in the width direction or a force intending to elastically recover to an original shape at both ends of the deflected correction plate (FIGS. 5 and 7) is applied to the deformed nail 20. This stabilizes a state of wearing the corrective device 15 on the deformed nail 20, preventing the corrective device 15 from dropping from the nail.

When a few days elapse after wearing a corrective device 15 on a deformed nail 20, the nail grows in a state of applying a restoring force of elasticity in a correction plate 16 to a deformed nail in the width direction, thereby eliminating deformation of ingrown nails, ingrown toenails and the like.

When a correction device 15 is released, a simple operation of curving a correction plate 16 in the deformation direction of a deformed nail 20 and pulling out the corrective device 15 in the direction of the nail tip can release the corrective device 15. Simple releasing is also derived from an effect of a hooked claw 17 provided at one edge of a correction plate 16.

Example 2

A SUS 304 stainless steel cold-rolled steel plate with a thickness of 0.8 mm was punched out to create an elastic metal strip 10 (FIG. 3) with four tongue strips 11 with a width of 1.5 mm and length of 5 mm protruding from the one edge of a correction plate 16 with a size of 22 mm×3 mm. After the tip of each tongue strip 11 was bent, each tongue strip 11 was further bent at a location 1 mm from the end of the correction plate 16 to form a hooked claw 17 with a double structure of a folding part 18 and a bending part 19.

Next, the product was heat-treated in a red hot condition at 500° C. for 30 minutes, followed by water hardening to remove stress and strain introduced in the bending process, as well as to improve hardness, and consequently elasticity of a corrective device 15.

A manufactured corrective device for a deformed nail 15 was applied to ten subjects to investigate the progress of correcting ingrown nails. A degree of correction varied with subjects, but the effect of correction was observed in about three days of wearing. In a fast case, there were subjects who completely eliminated ingrown nails when one week had elapsed, and ingrown nails were eliminated in almost everyone when two weeks had elapsed. After the corrective device 15 was released after elimination of ingrown nails, a nail tip and a finger tip were observed, and no abnormality due to the pressing of the corrective device 15 was found.

Next, a corrective device for deformed nails using a wrought wire rod is described in detail.

A wrought wire rod 30 (FIG. 9) is manufactured by cold processing such as rolling, casting and the like, in which an ordinary wire rod with circular cross-section is pressed to flatten in the direction of diameter. Since the wrought wire rod 30 is formed by cold processing, it is hardened to increase a recovery force of elasticity in comparison with a round wire rod. The wrought wire rod 30 may be treated as a cold-rolled plate on this point.

In a corrective device 35 for a deformed nail (FIG. 10) using a wrought wire rod 30 as a raw material, a hooked claw 37 is formed on both ends of a correction part 36 formed in a nearly dogleg shape when observed in plain view. The correction part 36 has a bending point 36a of the dogleg-shaped correction point located at the root side of deformed nail 20, forming a shape, in which both ends across the nail width are oriented to the direction of nail tip. The hooked claw 37 with a double structure of a folding part 38 and a bending part 39 is similarly formed by folding and bending the part protruded from both ends of the correction part 36 as a corrective device 15 using a cold-rolled plate as a raw material.

Figure 10:
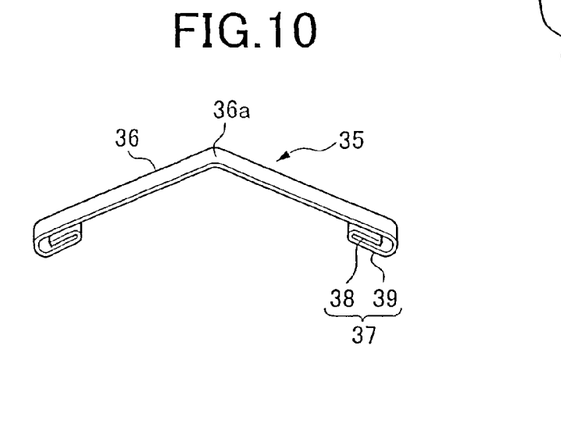
FIG. 10 is a perspective view of a corrective device using a wrought wire rod as a raw material.

A corrective device 35 using a wrought wire rod 30 as a raw material can be used to correct deformed nails without giving discomfort caused by a hooked claw 37 of cutting into a finger tip.

Figure 11:
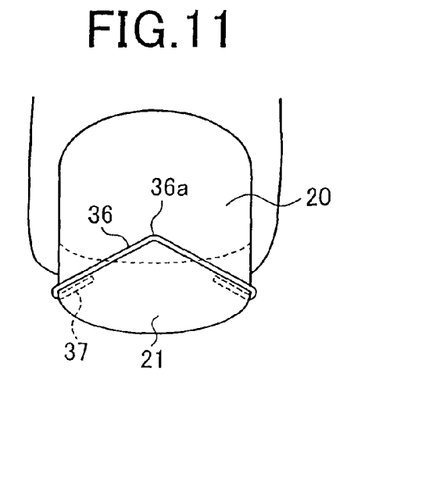
FIG. 11 is a plain view of a state of wearing this corrective device on a deformed nail.

By comparison, in a case using a round wire rod as a raw material, both ends of a wire rod are processed by spiral milling, to form a pinching part for retention, but a double spiral is required to obtain a pinch force to meet the object. However, a double spiral is likely to widen too much space between a finger tip and a deformed nail 20, for example, resulting in damaging socks with a double spiral when used to correct a toenail, leading to poor usability. In a corrective device 35 using a wrought wire rod 30 as a raw material, a step between a correction part 36 and a hooked claw 37 can be reduced in this respect and used safely since a sharp edge is not exposed to the outside. A double construction of a folding part 38 and a bending part 39 can further increase a pinch force and a corrective device 35 is thereby firmly worn on a deformed nail 20 (FIG. 11).

Example 3

A SUS 304 stainless steel cold-draw wire rod with wire diameter of 0.7 mm was cold-rolled to a thickness of 0.4 mm to collect a wrought wire rod with a length of 28 mm. Both ends of a correction part 36 were bent, followed by further bending at a location 2 mm from the tip of the fold to form a hooked claw 37 with a double structure of a folding part 38 and a bending part 39, which was finally bent in a dogleg shape with an open angle of 120 degrees, forming the shape in FIG. 10. The product after processing was heat-treated in a red hot condition at 500° C. for 30 minutes, followed by water hardening to remove stress and strain introduced in the bending process, as well as to improve hardness and consequently elasticity of a corrective device 35.

A manufactured corrective device for a deformed nail 35 was applied to ten subjects to investigate the progress of correcting ingrown nails. A degree of correction was varied with subjects, but the effect of correction was observed in about three days of wearing. In a fast case, there were subjects who completely eliminated ingrown nails when one week had elapsed, and ingrown nails were eliminated in almost everyone when two weeks had elapsed. After the corrective device 15 was released after elimination of ingrown nails, a nail tip and a finger tip were observed, and no abnormality due to the pressing of the corrective device 35 was found.

Next, a corrective device for deformed nails manufactured from a Cu—Al—Mn type shape-memory alloy is described in detail.

A corrective device for deformed nails manufactured from a Cu—Al—Mn type shape-memory alloy uses as a raw material a nearly rectangular metal band, which was collected by aligning its longitudinal direction with the rolling direction of a cold-rolled plate of a Cu—Al—Mn type shape-memory alloy with a recrystallization texture consisting of the substantially single phase having a uniform crystal orientation. Or a wire rod of a Cu—Al—Mn type shape-memory alloy with a recrystallization texture consisting of the substantially β single phase having a uniform crystal orientation may be pressed to flatten and then to cut out into a desired length for use as a raw material.

In a corrective device manufactured from a rectangular metal band, the width direction of the nail in a correction plate 16 is aligned with the longitudinal direction of the rectangular metal band and a tongue strip of forming a hooked claw 17 is protruded from the edge of the correction plate 16 near the tip similarly to corrective devices 15 in FIGS. 3, 5 and 7. In a corrective device manufactured from a wrought wire rod, the length direction of wrought wire is aligned with the width direction of the nail and bent to a dogleg shape similarly as a corrective device 35 in FIG. 10, forming a hooked claw 37 with a double structure of a folding part 38 and a bending part 39.

A corrective device using a cold-rolled plate of a Cu—Al—Mn type shape-memory alloy as a raw material utilizes a change of a shape involving the transformation and reverse transformation of a martensite.

A stress generated by the transformation and reverse transformation of a martensite in a shape-memory alloy conforms to the Claudius-Claperyon equation in the following formula (I). In the formula, a indicates an induced stress of the martensitic transformation or an induced stress of the reverse martensitic stress (Pa), T is temperature (K), ΔS is an entropy change in the transformation (J/m³·K), and ε is an amount of recovery strain, respectively.

$$d\sigma/dT = -\Delta S/\epsilon \tag{1}$$

A Claudius-Claperyon equation suggests an induced stress a in the transformation and reverse transformation of a martensite in a shape-memory alloy with a large entropy change in the transformation ΔS, and has large temperature dependency provided that an amount of recovery strain ε is at the same level. Therefore, it may be concluded that behavior with deformation stress in a corrective device manufactured from a shape-memory alloy substantially changes with a temperature change in living environments.

Figure 12:
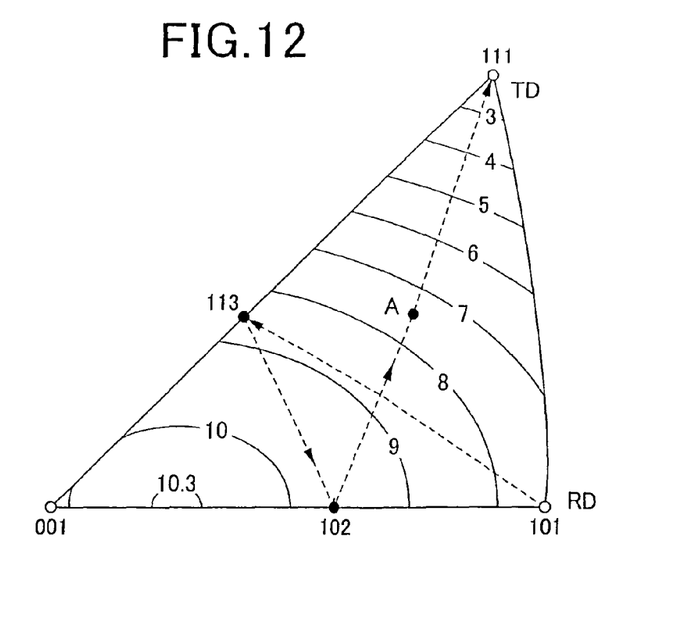
FIG. 12 is a graph illustrating directional dependency of an amount of strain in transformation of a single crystal of a Cu—Al—Mn alloy.

The shape-memory effect and super-elasticity effect in a shape-memory alloy largely depends on the crystal orientation in a single crystal. For example, a single crystal of a Cu—Al—Mn alloy shows an amount of recovery strain being 10% in the <100> direction, 7.5% in the <110> direction and 2% in the <111> direction, as shown in FIG. 12 representing the orientation dependency in an amount of the transformation strain, that is, an amount of recovery strain of the alloy. It may be concluded that the deformation stress becomes higher in the orientation with a smaller amount of the recovery strain ε at a certain temperature T, from the relation of the size in the amount of recovery strain corresponding to the crystal orientation with the equation (1). On the other hand, when a polycrystalline alloy has random crystal orientation, anisotropy is not observed in an amount of the recovery strain and the deformation stress, but orientation dependency similar to a single crystal occurs by formation of the aggregate texture.

The crystal orientation is herein briefly described.

Figure 13:
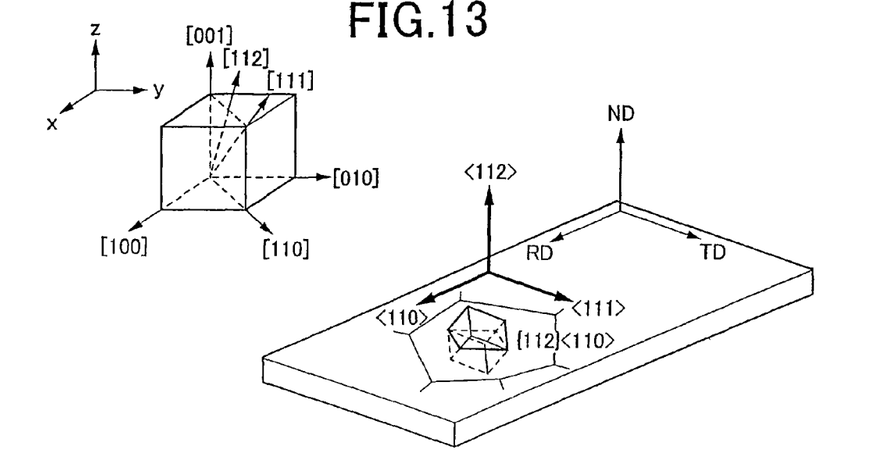
FIG. 13 is a diagram illustrating a representation method of the crystal orientation and the crystal orientation of a cold-rolled plate.

As a representation method of the crystal orientation, a method of defining the x-, y- and z-axes in relation to the unit crystal lattice of crystal structure by using the notation of [100], [010], and [001] orientations for each of them is common (FIG. 13). Various orientations based on these notations are expressed, for example, as [110], [111], and [112].

In a case of a single crystal of a shape-memory alloy, the crystal orientation determines an amount of the recovery strain due to the shape-memory effect and super-elasticity effect.

In a case of a rolling plate, the rolling direction, the width direction of the rolling plate and the direction normal to the rolling face are defined as RD, TD and ND, respectively. Since the TD direction is always specified in the <111> direction, an aggregate of the crystals with the crystal orientation of the <110> and <112> directions directed to the RD direction and ND direction, respectively, can be expressed as the {112}<110> aggregate texture. However, in case of the aggregate texture of polycrystalline substance, each crystal grain generates a certain level of the orientation distribution so that the mainly uniform orientation is defined as the principal direction for the oriented direction of aggregate texture.

Cu-based shape-memory alloys are known as shape-memory alloys with a small entropy change $\Delta S$ in the transformation and among them, a Cu—Al—Mn type alloy with excellent ductility is promising for a corrective device of the present invention since heat treatment can form the recrystallization aggregate texture with {112}<110> as the principal direction. That is, <110> and <111> of this alloy is mainly oriented in the RD direction and TD direction, respectively, so that the deformation stress becomes larger in the TD direction than the RD direction.

Cu—Al—Mn type alloys include a ternary system by a mass ratio of 3 to 10% Al, 5 to 20% Mn and Cu as the balance and impurities and an alloy, to which 0.001 to 10% as a whole of one or two kinds selected from Ni, Co, Fe, Ti, V, Cr, Si, Nb, Mo, W, Sn, Sb, Mg, P, Be, Zr, Zn, B, C, Ag and mish metal is added according to necessity (Patent Document 5).

Patent Document 5: Japanese Patent Publication No. 2001-20026A

A Cu—Al—Mn type alloy with the shape-memory effect and super-elasticity effect turns into the $\beta$ single phase (body-centered cubic) (b.c.c)) at high temperature and the two phase texture of $\beta+\alpha$ (face-centered cubic) (f.c.c)) at low temperature. Three percent or more of Al is required in order to form the $ single phase, but an excess amount of Al exceeding 10% is likely to embrittle a Cu—Al—Mn type alloy. An Al content is preferably set in a range of 6 to 10%. Addition of Mn enables the presence of the $\beta$ phase in a low Al content, improving the cold workability of a Cu—Al—Mn type alloy. Such an effect becomes evident in the presence of 5% or more of Mn, but its excess addition exceeding 20% has an adverse effect on the shape-memory effect and super-elasticity effect. A Mn content is preferably set in a range of 8 to 12%.

0.001 to 10% as a whole of one or two kinds selected from Ni, Co, Fe, Ti, V, Cr, Si, Nb, Mo, W, Sn, Sb, Mg, P, Be, Zr, Zn, B, C, Ag and mish metal, may be added as other addition components. Ni, Co, Fe, Sn, Sb and Be expresses reinforcement of a matrix, whereas Ti fixes N and O to render harmless. W, V, Nb and Mo are the components useful for improving the hardness and abrasion resistance. Cr improves the abrasion resistance and corrosion resistance, Mg increases the hot processability and toughness, and P and a mish metal are added as a deoxidizing agent to contribute to improving toughness. Zn also elevates transformation temperature of a martensite, B and C reinforce the grain boundary to improve processability and toughness, and Ag contributes to improve the cold processability.

A Cu—Al—Mn type alloy is used as a raw material of a corrective device to apply a stable corrective force to a deformed nail with very little change due to environmental changes over a long period of time. A cold-rolled plate with the aggregate texture is cut out in the rolling direction, which is aligned with the longitudinal direction of a correction plate, leading to small deformation stress in the RD direction (width direction of nail), but large deformation stress in the TD direction (direction of nail tip).

When a dogleg-shaped open angle is $\theta$ (degree) in a corrective device using a wrought wire rod as a raw material, the direction of hooked claw becomes the <110> direction, resulting in the width direction of the nail to be an angle rotated by 90 to $\theta/2$ (degree) from the RD direction to the TD direction. The relation of the orientation of a Cu—Al—Mn alloy with an amount of the transformation strain (FIG. 12) is similarly maintained in the Cu—Al—Mn type alloy, in which the aggregate texture is formed, changing an amount of the recovery strain depending on the orientation. A dotted line in FIG. 12 indicates the orientation, which is rotated within a rolling plane from RD to TD.

The point A is the orientation corresponding to rotation within a rolling plane by 70 degrees from the RD direction, where an amount of the strain in the transformation in this orientation becomes equal to that in the RD direction.

As recognized in FIG. 12, rotation from the RD direction to the TD direction in a range of 0 to 70 degrees increases an amount of the recovery strain and the larger the amount of recovery strain, the smaller the deformation stress is so that the deformation stress becomes smaller in the width direction of nail and larger in the direction of the nail tip. Therefore, a dogleg-shaped open angle $\theta$ is preferably set in a range of 40 degrees or more but below 180 degrees, further preferably set in a range of 40 to 150 degrees in order to stably insert a hooked claw 37 between a finger tip and a nail tip 21.

The relation of the crystal orientation with the width direction of the nail and the direction of the nail tip is optimized to yield the stable corrective force caused by the shape-memory effect or super-elasticity effect in relation to the width direction of the nail, being used for correction of deformed nails. The direction of action in the corrective force can be further controlled by treatment of the shape-memorization or treatment of super-elasticization so that the corrective force can be applied in an appropriate distribution in relation to the width direction of the deformed nail, enabling effective elimination of the deformation. On the other hand, a pinch force for retention of a nail tip 21 is enhanced by a double structure of hooked claws 17, 37 in relation to the nail tip direction with the large deformation stress so that corrective devices 15 and 35 are firmly worn on a deformed nail 20, as well as readily worn and released.

A corrective device for deformed nails manufactured from a Cu—Al—Mn type shape-memory alloy is manufactured through the following processes.

A Cu—Al—Mn type alloy with a desired composition is melted to cast to an ingot, which is processed by hot forging, cold rolling and the like to form a thin sheet, followed by the softening anneal at 500 to 700° C. to form a two phase texture of ($\beta+\alpha$). The cold rolling is preferably rolled in a multistep between an intermediate anneal in the two phase ($\beta+\alpha$) region and a total degree of process is preferably 30% or more, more preferably 50% or more. For example, when a copper type alloy of 82.2% Cu, 8.1% Al and 9.7% Mn is processed in a total degree of processing equal to 30% or more, the frequency of crystal orientation to the $ single phase present along the processing direction is 2.0 or higher, leading to noticeable anisotropy in the shape-memory effect, super-elasticity effect and deformation resistance.

When punching out or electric discharge machining a thin sheet after annealing, the longitudinal direction is aligned with the rolling direction to yield a nearly rectangular elastic metal strip 10 (FIGS. 3, 5 and 7). The elastic metal strip 10 has the length equivalent to or below the length of a deformed nail across the nail width and a plurality of tongue strips 11 is protruded from the edge near the nail tip. The position of the tongue strip 11 formed may be in the vicinity of the central part of the elastic metal strip 10 in the length direction (FIG. 3) or in the vicinity of both ends in the length direction (FIG. 5) or it may be formed at even intervals in relation to the length direction of the elastic metal strip 10 (FIG. 7).

A tongue strip 11 is folded and bent to form a hooked clip 17 with a double structure of a folding part 18 and a bending part 19 on the edge of correction plate near the nail tip. A tip of a tongue strip 11 is folded into the side of correction plate 16, forming a structure of pressing a deformed nail inserted between the hooked claw 17 and the correction plate 16 with the folding part 18. Deformation resistance is high because of a double structure of the hooked claw 17, preventing injury to a nail and a finger tip from the edge of the hooked claw 17.

A corrective device 15 formed in a desired shape is heat-treated to provide the shape-memory effect or super-elasticity effect.

In heat treatment, a corrective device is heated (solution treatment) up to a temperature range to form the β single phase and transform the crystal texture to the β single phase, forming the recrystallization aggregate texture. While a temperature of the β single phase region and a temperature of the two phase (β+α) region vary with the alloy composition, generally a temperature of the β single phase region and that of the two phase (β+α) region is in a range of 700 to 950° C. and 400 to 850° C., respectively. It is sufficient when a holding time at the temperature of the β single phase region is equal to or longer than 0.1 minute, but a holding time is preferably set in 0.1 to 15 minutes since a long holding time exceeding 15 minutes raises concern about an adverse effect such as oxidation and the like.

A state of the β single phase region can be frozen by quenching after solution treatment. Quenching used includes immersion in a refrigerant such as water and the like, mist cooling, forced air cooling and the like. When a cooling rate is low, the α phase is separated out, not allowing to maintain the crystal structure of the β single phase region. A cooling rate is preferably equal to or faster than 50° C./sec, and practically set in a range of 100 to 1000° C./sec.

After annealing, the 0 phase is stabilized by age hardening at a temperature of preferably 300° C. or lower (more preferably 100 to 250° C.). When an age hardening temperature is too low, the 0 phase is not sufficiently stabilized, possibly causing it to change the transformation temperature of a martensite when left at ambient temperature. When the age hardening temperature exceeds 250° C. by contrast, the α phase is separated out at the age hardening temperature, being inclined to drastic reduction of the shape-memory characteristics and super-elasticity. A period for age hardening is varied with a composition a Cu—Al—Mn type alloy, but chosen preferably to be between 1 and 300 minutes (more preferably 5 to 200 minutes). When an aging time is short, not reaching 1 minute, sufficient aging effect cannot be obtained, whereas when exceeding 300° C. by contrast, there is concern with reduction of the shape-memory characteristics and super-elasticity characteristics caused by separation of the α phase.

A corrective device is treated for the shape-memory and super-elasticity to show a large shape restoring force in the width direction of the nail while maintaining high deformation stress in the direction of the nail tip, so that the shape restoring force can be effectively utilized for correcting ingrown nails, ingrown toenails and the like, and the corrective device is firmly worn on deformed nails.

Large deformation stress relative to the direction of the nail tip prevents an angle between a hooked claw 17 and a correction plate 16 from widening when the hooked claw 17 is engaged with a nail tip 21 to wear a corrective device on a deformed nail 20, and to prevent the corrective device 15 from dropping from the deformed nail 20. The hooked claw 17 extended to the direction of the nail tip is effective to prevent the shape restoring action in the direction of the nail. Since the corrective device is further manufactured from a Cu—Al—Mn type alloy with a small entropy change in the transformation ΔS, an amount of variation in a restoring force is extremely small even with the environmental changes and material deterioration does not occur so that effective correction of a deformed nail becomes possible without causing a patient pain.

A corrective device for deformed nails using a wrought wire rod of a Cu—Al—Mn type alloy as a raw material is manufactured by a similar process. Specifically a Cu—Al—Mn alloy with a desired composition is melted to cast to an ingot, which is then processed by heat forging, cold wire drawing and the like to a round wire rod, followed by rolling to manufacture a wrought wire rod, which is finally processed by the softening anneal at 500 to 700° C. to form the two phase texture of (β+α). The cold wire drawing and cold rolling are preferably a multistep wire drawing and rolling involving an intermediate anneal in the two phase (β+α) region and a total degree of process is preferably 30% (more, more preferably 50% or more). For example, when a copper type alloy of 82.2% Cu, 8.1% Al and 9.7% Mn is processed in a total degree of processing equal to 30% or more, the frequency of crystal orientation to the 0 single phase present along the processing direction is 2.0 or higher, leading to noticeable anisotropy in the shape-memory effect, super-elasticity effect and deformation resistance.

A wrought wire rod after anneal is cut and both ends are folded and bent to form a hooked claw 37 with a double structure of a folding part 38 and a bending part 39 on both ends of the corrective plate 36 in the wide direction of the nail. Both apical ends are folded in the side of a correction part 36 to give a structure of pressing a deformed nail 20 inserted between the hooked claw 37 and the corrective part 36 with the folded part 38. Since the hooked claw 37 has a double structure, it has high deformation resistance, preventing injury to a nail and a finger tip from the edge of a hooked claw 37.

A wrought wire rod is bent at nearly midpoint to deform to form a dogleg shape before or after formation of a hooked claw 37. At this time, an open angle of a dogleg shape is preferably adjusted within 40 to 150 degrees.

A corrective device 35 formed in a desired shape is heat-treated to provide the shape-memory effect or super-elasticity effect. The condition for solution treatment and age hardening similar to the case using a cold rolled plate as a raw material is used in heat treatment.

A corrective device 15 or 35 provided with the shape-memory effect or super-elasticity effect is processed by surface treatment such as chemical treatment, plating, resin-coating and the like as needed. For example, formation of a hard film can improve scratch resistance of the corrective device 15 or 35, general coating including a metal skin such as Pd, Au, Ni, Ag, Cr and the like, a coating layer such as TiN and the like and ultraviolet electrodeposition coating can improve corrosion resistance and a coated film with an appropriate color tone can provide design novelty.

Example 4

In order to investigate anisotropy of a rolled plate, an ingot of a Cu—Al—Mn alloy with a composition by a mass ratio of 7.86% Al, 8.95% Mn, 3.1% Ni and Cu as the balance was hot-forged and annealed at 600° C. for the two phase (β+α)

region, followed by acid washing and cold rolling at 50% reduction to yield a cold-rolled plate with a thickness of 0.2 mm.

A cold-rolled plate was cut out by electric discharge machining to a rectangular metal band with a width of 3 mm and length of 50 mm such that its RD direction and TD direction of the plate were aligned with the longitudinal direction of the metal band, respectively. The rectangular metal band was solution-treated at 900° C. for 5 minutes, followed by water quenching and then age hardening at 200° C. for 15 minutes.

Figure 14:
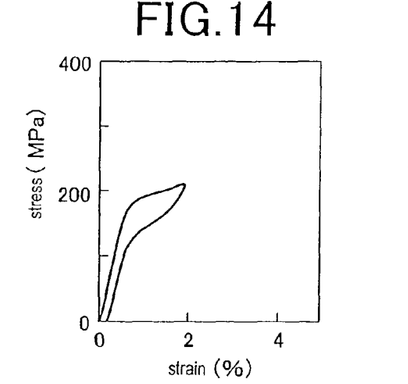
FIG. 14 is a stress-strain curve of a rectangular metal band obtained by cutting out a cold—rolled plate of a Cu—Al—Mn type shape-memory alloy annealed at 600° C. in the rolling (RD) direction.
Figure 15:
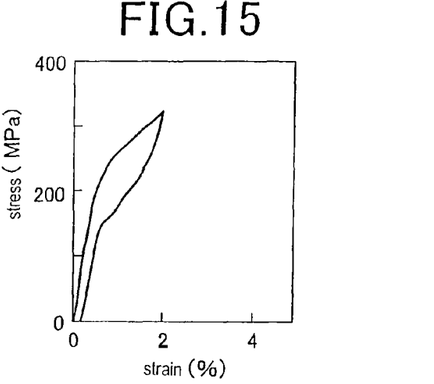
FIG. 15 is a stress-strain curve of a rectangular metal band obtained by cutting out a cold-rolled plate of a Cu—Al—Mn type shape-memory alloy annealed at 600° C. in the traverse (TD) direction.

Stress was applied to a rectangular metal band after age hardening to determine a stress-strain curve. Characteristics of the soft super-elasticity effect were obtained in the rectangular metal band in the RD direction having the <110> as the main orientation (FIG. 14), whereas the super-elasticity with high deformation stress was obtained in the rectangular metal band in the TD direction with the <111> orientation (FIG. 15). As apparent from this comparison, a cold rolled plate is cut out from a raw material of a corrective device such that the longitudinal direction (width direction of nail) of a correction plate 16 is consistent with the RD direction, thereby satisfying both corrective action on a deformed nail and wearing stability on a nail tip.

Reference Example 1

A cold-rolled plate of a Cu—Al—Mn alloy manufactured under the same condition as Example 4 except annealing at 900° C. for the β single phase region after hot forging was cut out to a rectangular metal band in the RD direction and TD direction, respectively.

Figure 16:
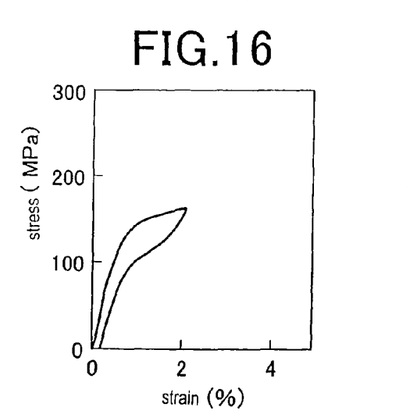
FIG. 16 is a stress-strain curve of a rectangular metal band obtained by cutting out a cold-rolled plate of a Cu—Al—Mn type shape-memory alloy annealed at 900° C. in the RD direction.
Figure 17:
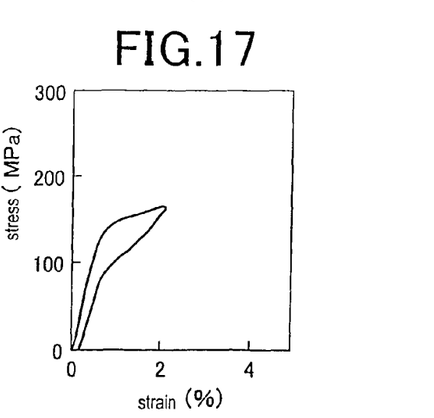
FIG. 17 is a stress-strain curve of a rectangular metal band from a cold-rolled plate of a Cu—Al—Mn type shape-memory alloy annealed at 900° C. and cut out in a TD direction of a cold-rolled plate.

Crystal grains of a rectangular metal band obtained were randomly oriented in both RD direction and TD direction and no substantial difference was observed between a stress-strain curve in the RD direction (FIG. 16) and a stress-strain curve in the TD direction (FIG. 17). Therefore, there was no substantial difference of the deformation stress in a correction plate 16 and with that of a hooked claw 17, even if a raw material for a corrective device is cut out as aligning the longitudinal direction with the RD direction.

Reference Example 2

Figure 18:
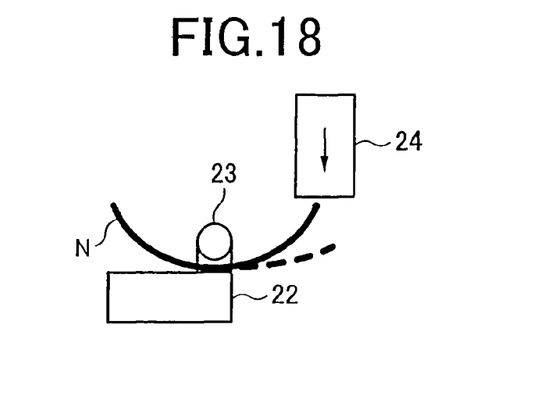
FIG. 18 is a schematic diagram of equipment measuring an amount of deflection of a nail strip proportionate to a load.

A bending behavior of a nail responding to the environmental changes was investigated to see the picture of an effect of the environmental changes such as temperature, humidity and the like on a nail of a human body. In a bending test, a nail strip N collected from a big toe was used, and one end of the nail strip N fixed with a holding member 23, on a pedestal 22, was pressurized with a weight 24 to determine the relation of a load with an amount of the deflection in the nail strip N when the nail strip N was pushed in (FIG. 18). Temperature dependency in atmosphere and water was also investigated after considering fluctuation of the nail strength by temperature, humidity and the like.

Figure 19:
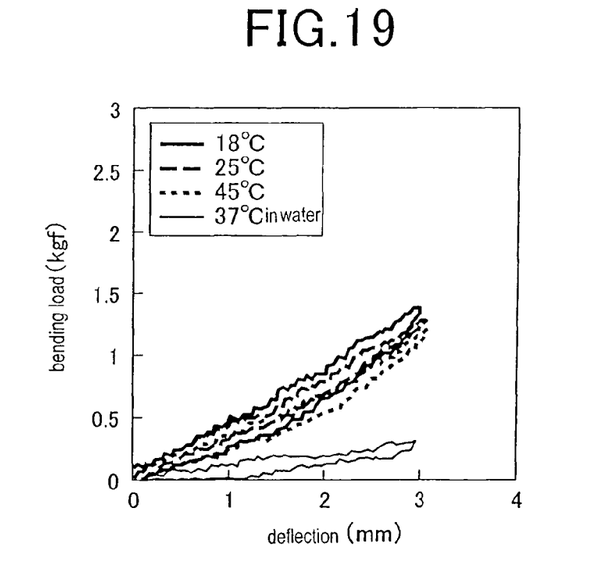
FIG. 19 is a bending load-deflection curve of a nail strip measured with the equipment in FIG. 18.

A typical bending load-deflection curve is shown in FIG. 19. Table 1 shows a bending load when the nail strip was pushed in 3 mm deep at each temperature in atmosphere and in water, and a rate of change with a load on the basis of 25° C. It is understood from FIG. 19 and Table 1 that a load in bending deformation is decreased, while not much, with a rise in a temperature in atmosphere and a load in bending deformation accompanied with temperature elevation is drastically decreased in water, and a load in bending deformation is slightly decreased when water temperature is further increased.

TABLE 1

Effect of environmental changes on nail strength

| | Measured temperature (° C.) | Load when pushed in 3 mm deep (kgf) | Rate of change with load (based on 25° C.) |
|---|---|---|---|
| In atmostphere (humidity: 20-40%) | 18 | 1.39 | 7.9 |
| | 25 | 1.28 | 0 |
| | 35 | 1.22 | −4.3 |
| | 45 | 1.12 | −11.5 |
| | 57 | 1.04 | −17.3 |
| In water | 15 | 0.36 | 8.3 |
| | 25 | 0.33 | 0 |
| | 37 | 0.29 | −11.1 |
| | 45 | 0.27 | −16.7 |

Example 5

Figure 20:
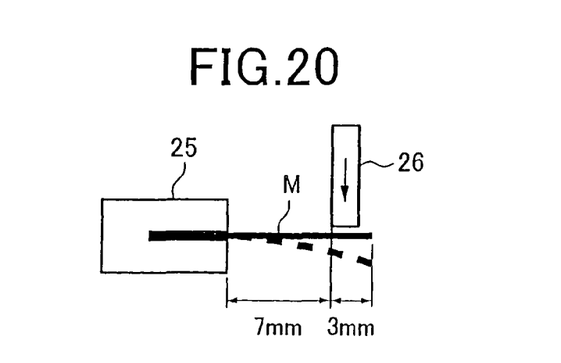
FIG. 20 is a schematic diagram of test equipment pressuring a rectangular metal band of a Cu—Al—Mn type alloy to determine a load in deformation recovery after releasing pressure.

A rectangular metal band with a width of 2.7 mm, length of 14 mm and thickness of 0.2 mm cut out from the same cold-rolled plate of a Cu—Al—Mn type alloy as Example 4 was used to investigate temperature dependency of a corrective force in a bending test. In the bending test, a rectangular metal band M was supported in a cantilevered state with a dice 25 and a weight 26 was placed on the rectangular metal band M at the end of the projecting part, 3 mm high to push in, evaluating a force when returning by 1 mm after releasing pressure as a correction force (load in deformation recovery) (FIG. 20). A correction force of a Ni—Ti alloy band was also measured in a similar bending test for comparison.

Figure 21:
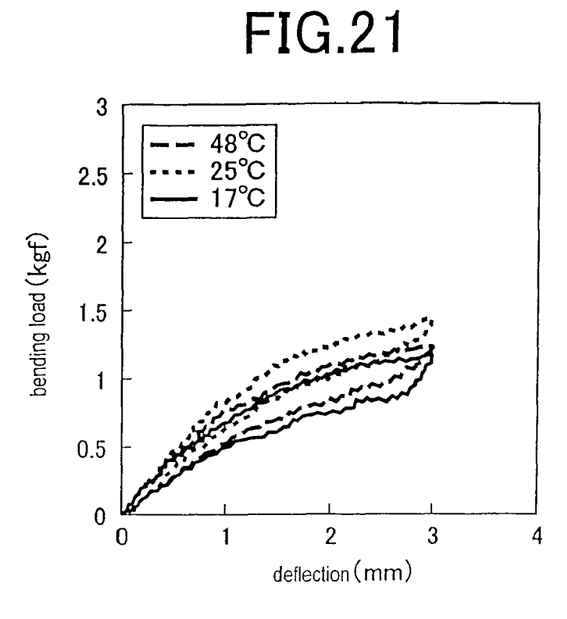
FIG. 21 is a bending load-deflection curve of a rectangular metal band cut out from a Cu—Al—Mn type alloy.

A rectangular metal band of a Cu—Al—Mn type alloy shows a bending load-deflection curve in FIG. 21 and varies a deformation load responding to an environmental temperature as shown in Table 2.

Figure 22:
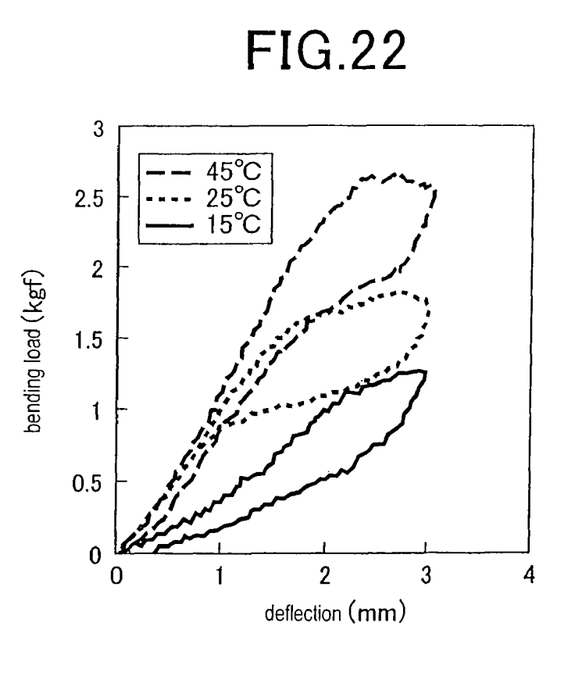
FIG. 22 is a bending load-deflection curve of a rectangular metal band cut out from a Ni—Ti alloy.

On the other hand, FIG. 22 and Table 3 show a bending load-deflection curve and a deformation load responding to an environmental temperature in a Ni—Ti alloy band, respectively. FIG. 22 and Table 3 indicate a bending-deflection curve responding to a temperature change is large in the Ni—Ti alloy band and the deformation load and the recovery load are drastically increased with raising the temperature.

Compared to this, it is understood that the deformation load and a load in deformation recovery slowly fluctuates with a temperature change in a rectangular metal band of a Cu—Al—Mn type alloy, and a rapid change with corrective force to cause pain does not occur.

TABLE 2

Temperature dependency of deformation load in Cu—Al—Mn type alloy

| Measured temperature (° C.) | Load when returning by 1 mm after pushing in 3 mm deep (kgf) | Rate of change in load (%) (based on 25° C.) |
|---|---|---|
| 5 | 0.6 | −27.7 |
| 17 | 0.75 | −9.6 |
| 25 | 0.83 | 0 |
| 38 | 0.95 | 14.5 |
| 48 | 0.99 | 19.3 |
| 58 | 1.11 | 33.7 |

TABLE 3

Temperature dependency of deformation load in Ni—Ti alloy

| Measured temperature (° C.) | Load when returning by 1 mm after pushing in 3 mm deep (kgf) | Rate of change in load (%) (based on 25° C.) |
|---|---|---|
| 6 | 0.31 | −71.67 |
| 15 | 0.5 | −54.1 |
| 20 | 0.98 | −10.1 |
| 25 | 1.09 | 0 |
| 35 | 1.44 | 32.1 |
| 45 | 1.68 | 54.1 |
| 56 | 1.85 | 69.7 |

Figure 23:
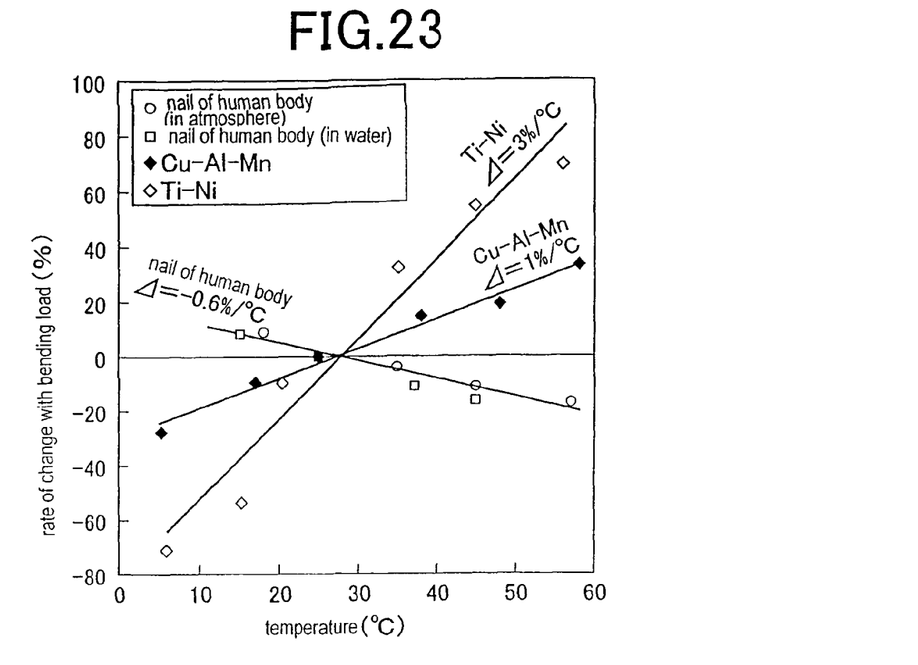
FIG. 23 is a graph comparing a rate of change of a deformation load with temperature in a nail of the human body, a Cu—Al—Mn type alloy and a Ni—Ti type alloy.

A rate of change in a deformation load with temperature (based on 25° C.) is about 1%/° C. in a Cu—Al—Mn type alloy and about 3%/° C. in a Ni—Ti alloy while about −0.6% in a nail of human body as found in comparison of a nail with a Cu—Al—Mn type alloy and a Ni—Ti alloy in FIG. 23. These results indicate there are extremely low fluctuations of a deformation load with a temperature change and no rapid change of a corrective force in a Cu—Al—Mn type alloy.

A nail of the human body is softened with temperature increase and humidity increase when wearing socks, shoes and the like or bathing and the like and it becomes extremely soft in particular in water. Therefore, a corrective force in a corrective device is drastically increased with temperature elevation, resulting in effective correction of a nail, but excess correction raises concerns about nail splitting. In this respect, a corrective device for deformed nails manufactured from a Cu—Al—Mn type alloy is low in temperature dependency of a deformation load, thereby stably and safely correcting deformed nails in the environmental changes.

Next, characteristics change with use environment was investigated in a Cu—Al—Mn type alloy with a composition by a mass ratio of 8.1% Al, 11.2% Mn and Cu as the balance.

An ingot was hot-forged, then annealed at 600° C., acid washed and cold-rolled at 70% reduction to manufacture a cold-rolled plate with sheet thickness of 0.2 mm. The rolling plate was cut out by electric discharge machining to a rectangular test strip with a width of 2.7 mm and length of 40 mm, which was subjected for solution treatment at 900° C. for 5 minutes, followed by quenching and solution treatment at 150° C. for 15 minutes for stabilizing the transformation temperature of a martensite.

Bending processability was investigated with a test strip left as heat-treated and a test strip left for a desired time in an environment test device of controlling the temperature and humidity. In a bending test, a bent part was inspected to grade the bending processability as "poor" when cracked at a curvature radius of 1 mm, as "average" when cracked in hairpin bend and as "good" when not cracked in hairpin bend. A coated test strip was similarly investigated for the bending processability in order to investigate an effect of coating. Each shape-memory alloy of Cu—Zn—Al, Cu—Al—Ni and Ni—Ti was used as a comparative material.

As shown in the results of investigation of Table 4, a test strip of a Cu—Al—Mn type alloy shows good bending processability regardless of being left under a humid atmosphere, or the presence or absence of coating and effect of use environment was not found. Test numbers 3 and 4 include a test strip of a Cu—Al—Mn type alloy plated with Pd and coated with a resin, respectively and keep sufficient bendability after an environmental test under further more severe condition than test number 2, confirming usefulness as a corrective device for safely and stably correcting a nail.

On the contrary, a test strip of a Cu—Zn—Al alloy left as heat-treated did not have sufficient bendability and further drastically lowered its bendability after an environmental test. A test strip of a Cu—Al—Ni alloy has poor bendability and a test strip of a Ni—Ti alloy could not obtain sufficient bendability, resulting in concern about stability when worn on a nail.

TABLE 4

Effect of environmental test and coating on bendability

| Test number | Alloy composition (by % mass) | Coating | Environmental test condition | | | Bendability |
| | | | Temperature (° C.) | Humidity (% relative humidity) | Holding time (hours) | |
|---|---|---|---|---|---|---|
| 1 | Cu: 80.7, | None | — | — | — | good |
| 2 | Al: 8.1, | None | 50 | 40 | 240 | good |
| 3 | Mn: 11.2 | Pd plated | 70 | 90 | 120 | good |
| 4 | | Resin coating | 70 | 90 | 120 | good |
| 5 | Cu: 69.5, | None | — | — | — | average |
| 6 | Zn: 24.5, Al, 6 | None | 50 | 40 | 240 | poor |
| 7 | Cu: 81.1, | None | — | — | — | poor |
| 8 | Al, 14.5, Ni: 4.4 | None | 50 | 40 | 240 | poor |
| 9 | Ti: 44.1, Ni: 55.9 | None | — | — | — | average |
| 10 | | None | 50 | 40 | 240 | average |

An ingot of a Cu—Al—Mn—Ni alloy with a composition by a mass ratio of 7.86% Al, 8.95% Mn, 3.1% Ni and Cu as the balance was hot-forged, annealed at 600° C., acid washed and cold-rolled at 50% reduction to yield a cold-rolled plate with sheet thickness of 0.2 mm. The cold-rolled plate was annealed at 600° C. for 15 minutes to then form a raw material for a corrective device (elastic metal strip 10) by electric discharge machining. A raw material for a corrective device has a shape of a correction plate 16 with a width of 3 mm and length of 21 mm, from which four tongue strips 11 with a width of 1.5 mm and length of 5 mm were protruded at the edge in the longitudinal direction (FIG. 3).

A tongue strip 11 was folded and bent to form a hooked claw 17 with a double structure of a folding part 18 and a bending part 19. The hooked claw 17 protruded from the edge of a correction plate 16 was set 3 mm long, whereas a gap of the hooked claw 17, into which a nail tip 21 is inserted was set 1 mm wide.

After forming a hooked claw 17, a corrective device was solution-treated at 900° C. for 5 minutes and then quenched to treat for age hardening at 200° C. for 15 minutes for stabilizing the transformation temperature of a martensite. A recrystallization aggregate texture of {112}<110> was formed in a Cu—Al—Mn—Ni alloy, which was provided with anisotropy in low deformation resistance but high shape-memory ability in relation to the RD direction, but high deformation resistance in relation to the TD direction.

For comparison, an ingot of a Cu—Al—Mn—Ni alloy with the same composition was hot-forged, annealed at 900° C., acid washed and cold-rolled at 20% reduction to manufacture a cold-rolled plate with a thickness of 0.2 mm and a corrective device with a similar size was prepared from the cold-rolled plate. In this case, similar heat treatment after forming a hooked claw 17 did not form a clear aggregate texture, but a nearly random metal texture so that deformation resistance with anisotropy was not provided.

Figure 24:
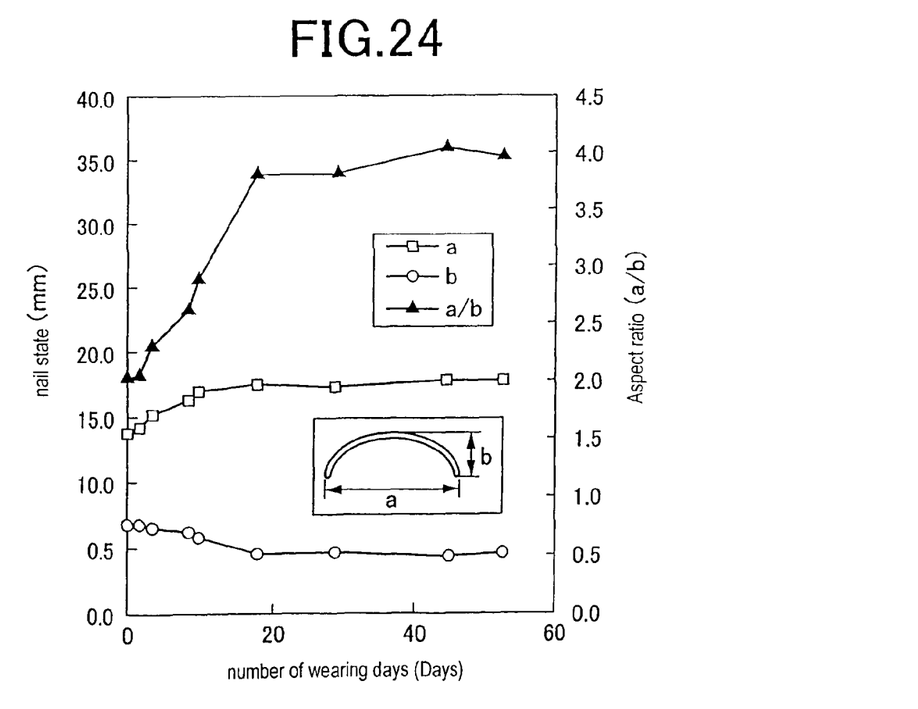
FIG. 24 is a graph representing correction ability of a corrective device for a deformed nail as a variation of a nail width a, a nail height b and an aspect ratio a/b with time.

A prepared corrective device for a deformed nail 15, was applied to ten subjects to investigate the progress of correcting ingrown nails. A degree of correction was varied with subjects, but when wearing a corrective device having anisotropy with the deformation resistance, no corrective device was dropped from a nail, a corrective effect was observed in about 3 days after wearing in the fast cases, there were subjects who completely eliminated ingrown nails when one week had elapsed, and ingrown nails were eliminated in almost everybody when three weeks had elapsed. FIG. 24 is a graph representing a degree of correcting a nail in certain subjects, as a variation of a nail width a and a nail height b with time. A shape of a nail gradually changed as the number of days of wearing a corrective device increased, resulting in a change of an aspect ratio a/b from 2.0 to 4.0 to broaden the nail width a. A convoluting state was eliminated with broadening of the nail width a to alleviate pain due to an ingrown nail. After eliminating an ingrown nail, a corrective device 15 was released to observe a nail tip and a finger tip, finding no abnormality caused by pressurizing the corrective device 15.

Compared to this, in a subject wearing a corrective device manufactured from a Cu—Al—Mn—Ni alloy heat-treated at 900° C., an angle between a correction plate 16 and a hooked claw 17 was broaden to loosen a correction plate upward, thereby frequently dropping a corrective device 15 from a nail 20. When a corrective device manufactured from a Cu—Zn—Al alloy was used, a similar trend was observed. In some case, a hooked claw 17 was broken and a corrective device 15 was dropped from a nail 20. Therefore, an ingrown nail was not corrected when two weeks had elapsed and almost all subjects still complained pain of from an ingrown nail when three weeks had elapsed.

Example 6

Figure 9:
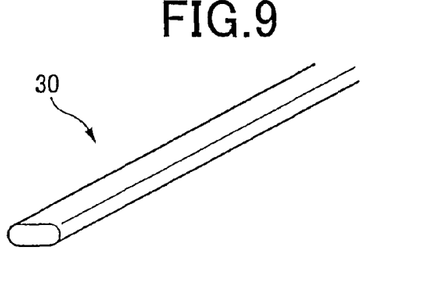
FIG. 9 is a partial perspective view of a wrought wire rod.

An ingot of a Cu—Al—Mn—Ni type alloy with composition by a mass ratio of 7.95% Al, 9.53% Mn, 2.08% Ni and Cu as the balance was hot-rolled with a grooved roll, cold-rolled with a grooved roll, annealed at 600° C., acid washed and cold wire-drawn at 75% reduction to form a wire rod with wire diameter of 0.7 mm. The wire rod was further annealed at 600° C. for 5 minutes to then cold-roll to a wrought wire rod with a thickness of 0.4 mm (FIG. 9). The wrought wire rod was cut to 28 mm long and both ends of a correction part 36 were bent to further bend at a location 2 mm from the tip of bending part to form a hooked claw 37 with a double structure of a folding part 38 and a bending part 39. The product was next bent in a dogleg shape with an open angle of 90 degrees (FIG. 10).

A corrective device 35 obtained was subjected to solution treatment at 900° C. for 5 minutes and then quenched to perform age hardening at 200° C. for 15 minutes for stabilizing the transformation temperature of a martensite. A recrystallization aggregate texture of {112}<110> was formed in a Cu—Al—Mn—Ni alloy, which was provided with anisotropy with low deformation resistance but high shape-memory ability in relation to the width direction of nail, and high deformation resistance in relation to the direction of the nail tip. For comparison, an ingot of a Cu—Al—Mn—Ni alloy with the same composition was hot-forged, annealed at 600° C., acid washed and cold-rolled at 50% reduction to form a cold-rolled plate with thickness of 0.2 mm, which was annealed at 600° C. for 15 minutes and then cut out by electric discharge machining to a dogleg shaped cold-rolled material with an open angle of 90 degrees.

Both ends of a dogleg shaped cold-rolled material were bent to further bend at a location 2 mm from the tip of bending part, to prepare a corrective device with a structure similar to one in FIG. 10. In this case, a recrystallization aggregate texture of {112}<110> was formed with the similar heat treatment after forming a hooked claw 37, but the width direction of nail became the RD direction and the direction of hooked claw became the direction rotated by 45 degrees from the RD to TD direction, so that anisotropy with deformation resistance in the direction of hooked claw smaller than that in the width direction of nail, is provided as predicted from orientation dependency in FIG. 12.

A manufactured corrective device for a deformed nail 35 was applied to ten subjects to investigate the progress of correcting ingrown nails. A degree of correction was varied with subjects, but when wearing a corrective device of the Example of the present invention with a wrought iron rod as a raw material, no corrective device was dropped from a nail, a corrective effect was observed in about 3 days after wearing in the fast cases, there were subjects who completely eliminated ingrown nails when one week had elapsed, and ingrown nails were eliminated in almost everybody when two weeks had elapsed. After eliminating ingrown nails, a corrective device was released to observe a nail tip and a finger tip, finding no abnormality caused by pressurizing the corrective device 35.

Compared to this, in a corrective device in Comparative Example, in which a cold-rolled plate was cut out into a dogleg shaped by electric discharge machining, an angle between a correction part 36 and a hooked claw 37 was broad to be loosened upward, thereby frequently dropping a corrective device 35 from a deformed nail 20. Therefore, ingrown nails were not corrected when two weeks had elapsed and almost all subjects still complained of pain from an ingrown nail when three weeks had elapsed.

INDUSTRIAL APPLICABILITY

As described above, in the present invention, a hooked claw 6 (17, 37) engaged with a nail tip 21 of a deformed nail 20 is provided with a double structure of a folding part 4 (18, 38) and a bending part 5 (19, 39). Deformation resistance of the hooked claw is high because of a double structure and a corrective device is firmly worn on a nail tip. Since the hooked claw is further formed on the edge near the nail tip or both ends across the nail width, a recovery force of elasticity in a correction plate 16, or correction part 36 in relation to the width direction of nail, and consequently correction ability for deformed nails is not reduced because of forming the hooked claw. A corrective device for deformed nails with an excellent capability of correcting deformed nails can thus be obtained, regardless of easy wearing and releasing.

What is claimed is:

1. A corrective device for deformed nails, the corrective device comprising:
    a correction portion to be positioned along a width direction of a nail; and
    a plurality of hooked claws extending from the correction portion and adapted to engage with a nail tip of the nail, wherein
    the correction portion and the hooked claws are formed from an elastic metal, and
    the hooked claws each have a double structure of a folding part and a bending part extending from the folding part, the bending part being folded back to be adjacent to the folding part.

2. The corrective device for deformed nails according to claim 1, wherein
    the correction portion is a correction plate having a plurality of tongue strips extending from an edge of the correction plate towards the nail tip, and
    the tongue strips form the hooked claws.

3. The corrective device for deformed nails according to claim 2, wherein
    the correction plate is a nearly rectangular elastic metal strip from a cold-rolled plate, and
    a longitudinal direction of the nearly rectangular elastic metal strip corresponds to the width direction of the nail.

4. The corrective device for deformed nails according to claim 2, wherein
    the hooked claws are spaced at even intervals along an entirety of the edge of the correction plate towards the nail tip.

5. The corrective device for deformed nails according to claim 2, wherein
    the hooked claws are spaced at even intervals at a central part of the edge of the correction plate towards the nail tip.

6. The corrective device for deformed nails according to claim 2, wherein
    the hooked claws are spaced at even intervals at opposite ends of the edge of the correction plate towards the nail tip.

7. The corrective device for deformed nails according to claim 2, wherein the correction plate is a nearly rectangular elastic metal strip from a cold-rolled material of a Cu—Al—Mn type shape-memory alloy with a recrystallization texture having a substantially β single phase with uniform crystal orientation in a rolling direction as a longitudinal direction, and
    the longitudinal direction of the nearly rectangular elastic metal strip corresponds to the width direction of the nail.

8. A manufacturing method for a corrective device for deformed nails according to claim 7, the manufacturing method comprising:
    forming the nearly rectangular elastic metal strip such that the tongue strips extend from the edge of the correction plate towards the nail tip by aligning the longitudinal direction with the rolling direction of a rolled-plate of the Cu—Al—Mn type shape-memory alloy that has been annealed;
    forming the hooked claws by folding and bending the tongue strips to create the folding parts and the bending parts; and
    after the forming of the hooked claws, heat treating the corrective device for shape-memorization or super-elasticization to orient a principal direction of the recrystallized β phase to the $\{112\}<110>$ orientation.

9. The corrective device for deformed nails according to claim 1, wherein
    the correction portion is a correction part having a protruding part extending from each of opposite ends of the correction part, and
    the protruding parts form the hooked claws.

10. The corrective device for deformed nails according to claim 9, wherein the correction part is a nearly dogleg shaped wrought wire rod.

11. The corrective device for deformed nails according to claim 9, wherein
    the correction part is a dogleg shaped wrought wire rod from a cold-pressed, flattened wire rod of a Cu—Al—Mn type shape-memory alloy with a recrystallization texture having a substantially β single phase with uniform crystal orientation.

12. A manufacture method for a corrective device for deformed nails according to claim 11, the manufacturing method comprising:
    forming a wrought wire rod by cold-pressing to flatten a wire rod of the Cu—Al—Mn type shape-memory alloy having been annealed;
    forming the wrought wire rod into a dogleg-shape to form the dogleg shaped wrought wire rod;
    forming the hooked claws by folding and bending the protruding parts extending from the opposite ends of the correction part to create the folding parts and the bending parts; and
    after the forming of the hooked claws, heat treating the corrective device for shape-memorization or super-elasticization to orient a principal direction of the recrystallization β phase to the $\{112\}<110>$ orientation.

13. The corrective device for deformed nails according to claim 1, wherein
    the folding part and the bending part of each of the hooked claws are positioned to be on a same side of the nail.

14. The corrective device for deformed nails according to claim 1, wherein
    the bending part of each of the hooked claws is linear.

15. The corrective device for deformed nails according to claim 1,
    wherein a free end of the bending part is in contact with the folding part for each of the hooked claws.

* * * * *